Feb. 4, 1958 P. F. DE VOR Plant Pat. 1,678
PINK ROSE PLANT
Filed June 25, 1957
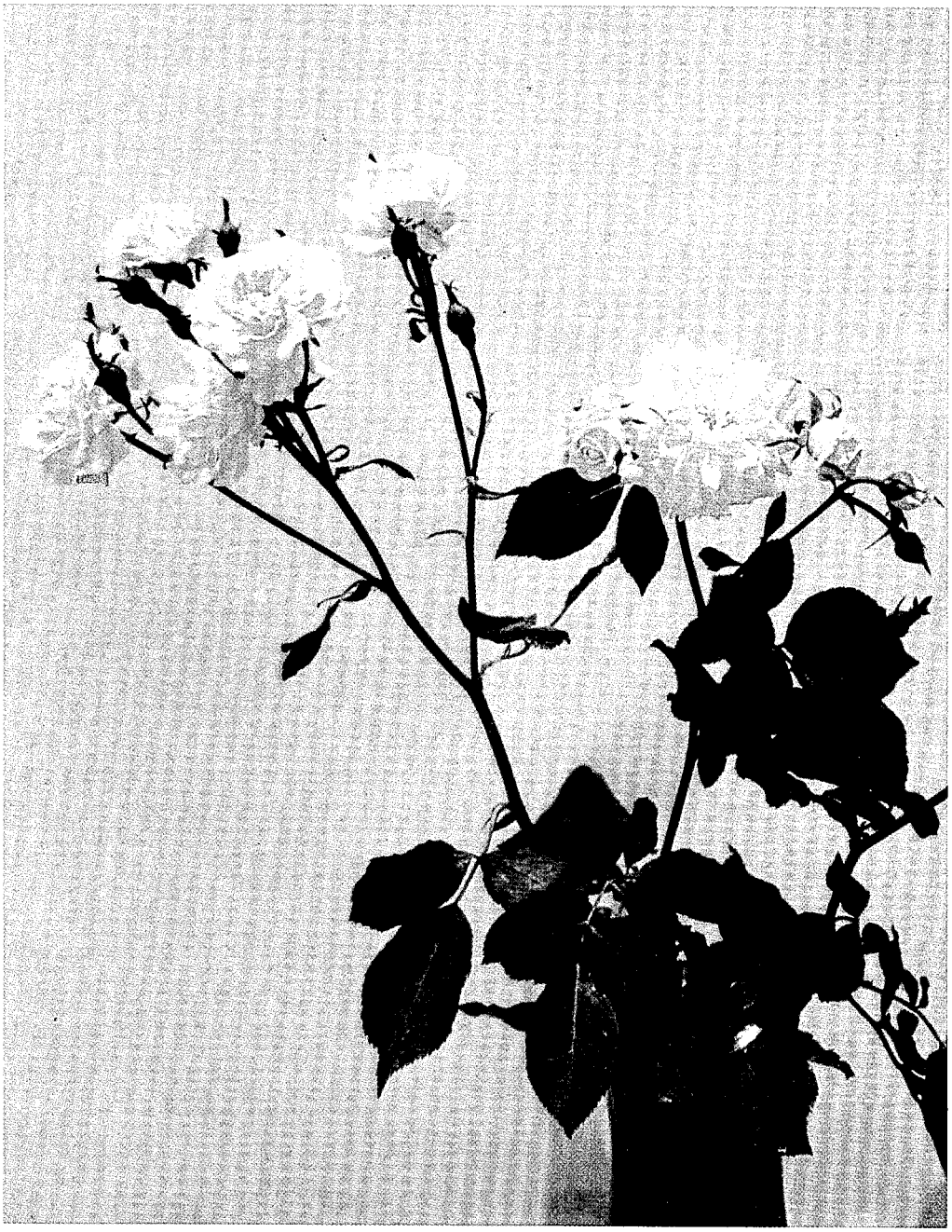
INVENTOR:
PAUL F. DeVOR
BY Rummler & Lucow
ATT'YS United States Patent Office Plant Pat. 1,678
Patented Feb. 4, 1958

1,678

PINK ROSE PLANT

Paul F. De Vor, Pleasanton, Calif., assignor to Clarence Amling Roses, Inc., Santa Ana, Calif., a corporation of California Application June 25, 1957, Serial No. 668,007

1 Claim. (Cl. 47—61)

The new variety of rose plant herein described and illustrated is a sport of the well-known rose "Carol Amling" (Plant Patent No. 1,126), discovered by me at Livermore, California. My new variety has been asexually reproduced under my direction at Livermore, California by budding and its characteristics appear to be permanently fixed.

The novelty of my new rose variety resides primarily in the lovely urn-shaped, high centered bud; the large number of flowers in each cluster; its vigorous growth; the relative thornlessness of the new variety, especially as regards flowering branchlets which are practically thornless; and the larger size of plant and its more spreading habit.

The accompanying illustration is a full color photograph showing two clusters of the flowers, together with stems and foliage, of the new variety. The flowers are shown in various stages from bud to full bloom and the colors shown are substantially true to the color designations hereinafter mentioned.

The following is a detailed description of my new variety of rose plant and any color designations therein are according to the Horticulture Color Chart of the British Colour Council:

Classification: Botanic—hybrid polyantha. Commercial—floribunda.

*Flower*

Blooming habit: Continuous. Blooms profusely early, midseason and late.
Size: Diameter, 2¼–2½ inches. Depth, ¾–1 inch.
Borne: In clusters. 3–15 and occasionally up to 25.
Shape: High center, regularly imbricated. At a later-stage form flattens and center is irregularly imbricate.
Petalage: 55 to 65 petals plus many petaloids.
*Form.*—Ovate; outer petals often serrated with 2 or 3 indentations 1/16 inch deep.
*Color.*—Outer and inner petals—Rhodamine Pink (527/2). Base—Primrose Yellow (601/3) shading to 527/3, margins fading to almost white as flower ages. Reverse side—Rose Pink (427/2) shading to Primrose Yellow (601/3) at base. Petals remain on stems 5–7 days.
Petaloids: 25 to 32.
*Color.*—Same as petals.
*Size.*—⅛ x ⅝ to ⅜ x 1 inch long.
Peduncle:
*Length.*—1¼–2". Sturdy and upright.
*Color.*—Pod Green (061) heavily tinged with reddish brown anthocyanin pigment toward base.
Discoloration (after full bloom): Fades to Rhodamine Pink (527/3) shading to white. In hot weather the color fades more rapidly.
Texture: Soft.
Appearance: Satiny.
Persistence: Hangs on and dries.
Fragrance: Very slight.
Lasting quality: On plant, 4–5 days. As a cut flower, 5–6 days.

*Bud*

Size: ⅞–1⅛ in. high.
Form: High centered.
Shape: Urn.
Diameter: ⅞–1⅛ inches.
Depth: ⅞–1⅛ inches. Opens slowly.
Color: When sepals first divide and petals begin to unfurl—Rhodamine Pink (527/2).
Sepals: Spear-shaped and curl back. Color: inside—Lavender Green (000761/2); outside—Lettuce Green (861) tinged with brownish red anthocyanin at margins.
Calyx: Funnel shaped.
*Size.*—Small. Does not split.
*Aspect.*—Smooth. Margins of sepals have glandular hairs.
Peduncle: Length, 1¼–2 inches. Erect and rather slender. Smooth except for occasional gland-tipped hairs. Color—same as described above for flower.

*Plant*

Form: Medium sized bush.
Height: 3½–4 feet.
Growth: Upright, sturdy, and very vigorous.
Branching: Profuse.
Strength: Very strong grower.
Foliage: Abundant quantity.
*Number of leaves.*—3 per foot of stem.
*Size of leaf.*—3–3¾ x 4–6 inches.
*Shape.*—Elongate.
*Texture.*—Glossy and smooth; serrated.
*Color.*—Upper side—near Spinach Green (0960). Under side—Sage Green (000861).
*Leaflets.*—Terminal leaflet varies from 1⅛ x 1¾ to 1⅜ x 2⅛ inches. Number, usually 5 per leaf, occasionally 6 or 7.
*Petioles.*—Length, ¾–1 inch.
*Ribs and veins.*—Prominent.
*Rachis.*—Free of thorns and prickles. Plant has thorns and prickles, but relatively few. Color—light green. Size—large ones ⅜–½ inch long. Prickles occasionally on smaller branchlets; reddish brown in color.

*Genital organs*

Anthers:
*Arrangement.*—Irregular.
*Length.*—1/16 inch long.
*Number.*—Very few, 15–20.
Filaments:
*Length.*—1/16–3/16 inch.
*Color.*—Aureolin (3).
Pollen: Color—Aureolin (3–3/2).
Pistils:
*Number.*—25–35.
*Length.*—⅜–½ inch.
Stigmas: Color—Canary Yellow (2/3).
Characteristics of ovaries: Small, elongate, silvery haired.
Fruit: Slightly fertile.
*Shape.*—Round.
*Color at maturity.*—Yellow.

The open flower of this new variety is similar in color and irregularly imbricate flower-shape, to "Carol Amling" (Plant Pat. No. 1,126) but the buds are beautifully urn-shaped and high centered instead of ovoid. The flowers in the clusters of this species are arranged informally on pedicles growing at various divergent angles instead of more formally and compactly as in "Carol Amling" whose flowers are on longer pedicles and peduncles curving upward toward the center of the flower cluster. Consequently the central flowers in the clusters of this variety are usually higher than the axiliary ones, instead of all flowers being at about the same height as in the relatively flat-topped clusters of "Carol Amling."

There are more flowers per cluster in this new variety than is characteristic of "Carol Amling," as this new variety has from 3 to 15 and occasionally up to 25 flowers per cluster; whereas "Carol Amling" usually has 3 to 5 and occasionally up to 9 flowers per cluster. This variety also has more flowers occurring singly than its parent plant. However, fewer flowers of this sport are open at the same time in comparison to its parent plant which has a more determinate type of inflorescence.

The leaves of this new variety are from ¾ inch to 1 inch longer and proportionally wider than those of "Carol Amling" but fewer occur per foot of stem. Accordingly the plants of this new variety which are taller appear more open and less densely foliated. The leaves of this variety are also less heavily colored with purple red anthocyanin pigment.

Another distinctive characteristic of this new variety over its parent plant is that it is significantly larger and somewhat more spreading in habit. This variety is also relatively thornless compared to "Carol Amling" which is quite thorny.

The new variety is outstandingly different from "Garnette" (the unpatented parent of "Carol Amling") in such plant habits as being taller, having a more open type of growth, a relative lack of anthocyanin pigmentation, thornlessness, and less compact flower clusters, than is "Carol Amling" which has a greater resemblance to the "Garnette" ensemble of plant characteristics and differs from it mainly in flower color and form.

This new variety of rose plant is in most respects distinctively different from its parent variety and as herein described has many features tending to give it excellent decorative and commercial value.

Having thus disclosed my new discovery, I claim:

A new and distinct variety of rose plant, substantially as described, being characterized as to novelty by the depth, brilliance and Rhodamine Pink color of the blooms, its profuse blooming habit early, midseason and late, the size of the flowers and the large number of flowers per cluster, the good keeping quality of the flowers, its high-centered and urn-shaped bud, the healthy, vigorous growth of the plant, and its relative thornlessness.

No references cited.